(12) United States Patent
Stepenoff et al.

(10) Patent No.: US 8,574,887 B2
(45) Date of Patent: Nov. 5, 2013

(54) PROCESS TO GROW AND CONCENTRATE ALGAE

(75) Inventors: Gary Scott Stepenoff, Phoenix, AZ (US); Karin L. Hastings, Goodyear, AZ (US)

(73) Assignee: Core Intellectual Properties Holdings, LLC, Goodyear, AZ (US)

( * ) Notice: Subject to any disclaimer, the term of this patent is extended or adjusted under 35 U.S.C. 154(b) by 524 days.

(21) Appl. No.: 12/927,619

(22) Filed: Nov. 19, 2010

(65) Prior Publication Data

US 2011/0124089 A1    May 26, 2011

Related U.S. Application Data

(60) Provisional application No. 61/281,707, filed on Nov. 20, 2009.

(51) Int. Cl.
  *C12N 1/00*    (2006.01)
  *C12N 1/02*    (2006.01)
  *C12N 1/12*    (2006.01)
  *C12N 1/20*    (2006.01)

(52) U.S. Cl.
  USPC .................. 435/257.1; 435/243; 435/252.1; 435/261

(58) Field of Classification Search
  None
  See application file for complete search history.

(56) References Cited

U.S. PATENT DOCUMENTS

| 3,645,040 A | 2/1972 | Ort |
| 4,675,114 A | 6/1987 | Zagyvai et al. |
| 2011/0253623 A1 | 10/2011 | Hastings |

OTHER PUBLICATIONS

International Search Report and Written Opinion issued Nov. 23, 2011 for PCT/US2011/038006 filed May 25, 2011 (Inventor—Karin L. Hastings // Applicant—Mineral Biosciences LLC) (11 pages).
Yoon JH, et al., (2003) Paenibacillus kribbensis sp. nov. and Paenibacillus terrae sp. nov., bioflocculants for efficient harvesting of algal cells. International Journal of Systematic and Evolutionary Microbiology. 53: 295-301.
Kryder LR. (2007) Microalgae for Wastewater Treatment and Reuse. Available at http://www.leslieconsulting.com/docs/MicroalgaeForWastewaterTreatmentAndReuse.pdf (10 pages).

*Primary Examiner* — Debbie K Ware
(74) *Attorney, Agent, or Firm* — Ballard Spahr LLP

(57) ABSTRACT

A method to grow and concentrate algae by adding a bacterium to an aqueous algal solution. After the bacteria are added, the algae and bacterial precipitate out of solution and produce a viable algal concentration that is 30 to 45 percent algae by wet weight.

1 Claim, No Drawings

PROCESS TO GROW AND CONCENTRATE ALGAE

This application claims priority based on provisional application Ser. No. 61/281,707, filed Nov. 20, 2009.

This invention relates to growing and concentrating algae.

In another respect, the invention relates to agglomerating algae using a biological substance.

In a further respect, the invention relates to the bio-agglomeration of algae which minimizes harm to the algae.

In still another respect, the invention relates algal culture which utilizes bacteria in conjunction with algae.

Cultivation of algae has been pursued for many years. Those skilled in the art have long endeavored to improve algae production methods. Therefore it is desirable to develop new and improved procedures of algal culture to grow and concentrate algae.

Accordingly, it is a principal object of the invention to provide new and improved procedures for growing and concentrating algae.

This and other and further and more specific objects and advantages of the invention will be apparent to those skilled in the art from the following detailed description thereof.

We have discovered an improved method to grow and concentrate algae. The method includes the steps of providing a nutritional composition including nutrients for algae; and, preparing an aqueous solution of algae by growing algae in water in a first container while exposing the aqueous suspension to sunlight and adding the nutritional composition to the water in the first container. The first container has a bottom. The method also includes the steps of preparing an suspension of algal-agglomeration bacteria by growing bacteria in a second container; discontinuing the addition to the first container of the nutritional composition; admixing the aqueous solution of the algal—agglomeration bacteria to the aqueous solution of algae in the first container to produce an algal-bacterial aqueous solution and continuing to expose the algal-bacterial aqueous solution to sunlight to concentrate algae at the bottom of the first container; and, concentrating algae from the bottom of the container 12 to 72 hours after the algal-agglomeration bacteria is admixed to the aqueous solution of algae.

The following example is provided by way of description, and not limitation, of the invention.

EXAMPLE

Bacteria are grown in water in a first container. The presently preferred bacteria have not been genetically modified, but of course, genetically modified bacteria can be used if desired. These bacteria have several important physical properties; namely, they are not predatory to the algae utilized, they are facultative anaerobic bacteria, and they have a symbiotic relation with the algae utilized and can co-exist with the algae without harming the viability of the algae. With respect to the viability of the algae, it appears that the algae utilized in the invention maintain normal growth, respiration, and other physiological and physical properties in the presence of the bacteria. Even though it is possible that a variety of other bacteria might find use in the practice of the invention, each of these physical properties is presently preferred in the practice of the invention. By way of example and not limitation the presently preferred bacteria are from the Class Bacilli and Order Bacillales. Paenibacillus 77 from the family Paenibacillaceae has been utilized in one embodiment of the invention.

The bacteria are grown until there is a concentration in the range of 0.5 e6 c/mL to 10.0 e6 c/mL is achieved.

Algae are grown in water in a 70,000 gallon pond which is twenty-two feet wide and 200 feet long. The depth of the pond is in the range of twelve to forty-eight inches. The size and depth of the pond can vary as desired; however, a depth greater than forty-eight inches is not preferred because the amount of sunlight reaching the bottom of the pond diminishes with depth. In particular, one of the advantages of the algae is that it can be grown and harvested at commercial scale, i.e., in tanks with a capacity of 5,000 to 1 million gallons or more, preferably at least 60,000.

A pump circulates water in the pond. The inlet to the pump is located in one side of the pond beneath the surface of the water in the pond. The inlet is presently preferably near the bottom of the pond. The outlet through which water is returned to the pond is located above, at, or below the surface of water in the pond. Water leaves the pond through the inlet, passes through the pump, and returns to the pond at the outlet. Water entering the pond through the outlet generates circulation of at least some of the water in the pond. Multiple inlets and outlets can, if desired, be provided. The capacity of the pump can vary as desired, but is presently in the range of 100 to 200 gallons per minute. The purpose of the pump is not to create great turbulence in water in the pond, but is to promote a low, gradual circulation of water in the pond. Excessive turbulence can injure the algae. The pump ordinarily runs during daylight hours and not during the night.

The surface of the water in the pond is open the ambient air and is exposed to sunlight during the day. If desired, a transparent cover can be provided for the pond. The daytime ambient temperature can be in the range of 70 degrees F. to 110 degrees F., but is preferably in the range of 80 degrees F. to 95 degrees F., The temperature of the water in the pond is in the range of 60 degrees to 100 degrees F., preferably in the range of 70 degrees to 95 degrees F. Small round fresh water algae from the Chlorella, Scenedesmus, Nannochloris, Chlamydomonas, and Chlorococcum, Euglena, Cryptomonas, and Ellipsoidion, these genera are presently preferred, although algae from other genera may be acceptable. While the algae are being grown in water in the growth vessel, nutrients are added to the water to feed the algae. The nutritional composition ordinarily is in a liquid form and can be added periodically to water in the pond but presently is continuously fed into water in the pond at a rate in the range of 200 to 400 gallons per day. The compositions of nutrients for algae are well known and, by way of example, typically include 6% to 15% by weight nitrogen, 5% to 35% by weight phosphate, and 1% to 6% by weight potassium. About 200 to 400 gallons of algal food is added to the 70,000 gallon pond each day. About 100 to 2500 gallons of water is added to the pond each 70,000 gallon pond each day to compensate for water lost into the atmosphere by evaporation and by the harvesting process.

The algae are allowed to grow in the pond until the algae concentration is over 1 million cells per mL. This aqueous algal concentration when dried produces algae solids that are 0.4% to 0.9% by weight of the aqueous algal concentration.

After the desired concentration of algae in the pond is achieved, 200 to 5000 gallons of the aqueous bacteria solution are added to the water in the algae pond. As noted, the concentration of the bacteria in the aqueous bacteria solution is in the range of 0.5 e6 cfu/mL to 10 e6 cfu/mL. The bacteria solution is dispersed on the entire pond surface using, by way of example and not limitation, a sprinkler system. As soon as the bacteria solution is added to water in the 70,000 gallon pond, the algal nutritional composition are no longer added to water in the pond. In developing the invention, we found this important because the bacteria should not be allowed to overwhelm the algae. After the bacteria are added to the 70,000 gallon pond, they function as biological agglomerate by attaching to algae and sinking to the bottom of the pond along with the algae. By way of example, about twelve hours after the bacteria are added to the 70,000 gallon pond, approximately three to eight percent of the algae present may have settled to the bottom of the pond. After twenty-four hours, approximately only half of the algae in the pond may have settle to the bottom of the pond with bacteria. Approximately eighteen hours after the bacteria are added, the precipitation of algae begins to take off. Consequently, algae preferably are concentrated from the bottom of the pond 12 to 72 hours, preferably 36 to 48 hours, after the bacteria solution is added to the pond. It is not desirable to wait more than 72 hours to concentrate the algae from the bottom of the pond because once the algae are on the bottom of the pond they are shielded from sunlight, and, because the addition of nutrients to the pond was discontinued when the bacteria were added. After 12 to 72 hours, the concentration of algae on the bottom of the 70,000 pond is typically in the range of 5% to 45% by wet weight. The concentration of algae on the bottom of the pond after it has been concentrated and is ready for harvest is at least 5 percent by wet weight, preferably at least 10 percent by wet weight, more preferably at least 20 percent by wet weight, and most preferably at least 30 percent by wet weight. As used herein, the time of concentration is the amount of time elapsed after bacteria are added to the pond until the time the algae is harvested. The time of concentration, as noted above, preferably 36 to 48 hours but can vary as desired.

The pH of the water in the 70,000 gallon pond during the initial growth of the algae and after the aqueous bacterial suspension is added to the pond is 7 to 12, preferably 8 to 11, and most preferably 9.5 to 10.5.

The proportion of algae in the 70,000 gallon pond that can be agglomerated and removed can be varied depending on the concentration of bacteria initially administered to the pond. As the concentration of bacteria administered initially to the pond is increased, the proportion of algae that is agglomerated and sinks to the bottom of the pond increases. As the amount of bacteria initially administered to the pond decreases, the proportion of algae that are agglomerated by the bacteria decreases, and it becomes more likely that some algal agglomerates are formed which have a specific gravity of one or less. If desired, bacteria can be added to the pond on more than one occasion.

One important advantage of the invention is that algae remain viable after they are harvested. In one preferred method of harvesting the algae, water is decanted from the 70,000 gallon pond, and a paste/concentrate is left behind in the pond container. The paste/concentrate is substantially comprised of viable algae. The paste/concentrate is removed using a mechanical system that does not break apart or harm the agglomerated algae or lyse cells. When the mechanical means is used, care is taken to not apply more than 100 gravities or excessive heat and pressure during harvesting of the agglomerated algae. For example, a temperature in excess of 212 degrees F. is not applied to the algae and a pressure not in excess of 250 psi is not applied to the algae. After the agglomerated algae are removed from the bottom of the container, further mechanical concentration by centrifugation or other means can be performed to remove water and increase the algae concentration. During such further mechanical centrifugation, it is important to maintain the viability of the algae. By way of example and not limitation, one mechanical means that can be used to remove agglomerated algae from the bottom of the container is to use a slow running pump and filtration system that would suction agglomerated algae from the bottom of the container at a rate in the range of 2 to 10 gallons per minute.

One surprising result of the above described algal growth, agglomeration, and harvest system of the invention is that the particular bacteria discovered and utilized do not appear to harm the algae and that; instead, the algae maintain viability while the bacterial agglomerate the algae.

Another surprising result of the algal system of the invention is that the algal agglomerate which is produced has a specific gravity greater than one.

A further surprising result of the algal system of the invention is that the algae which are not agglomerated by the bacteria and which remain in the pond retain their viability and function normally.

Still another surprising result of the algal system of the invention is that the bacteria appear to improve the quality of byproducts produced during processing of the concentrated algae. Such byproducts include increased lipid production and increased native protein yields.

Still a further surprising result of the algal system of the invention is that the capital cost of concentrating alga is small compared to established industry standards.

Yet another surprising result of the algal system of the invention is that the operational cost of concentrating algae is small compared to established industry standards.

Yet still another surprising result of the algal system of the invention is that a system for concentrating algae from a large production pond has significantly reduced the cost of concentrating and harvesting algae.

Having described our invention in such terms as to enable those skilled in the art to understand and practice it, and having described the best mode thereof, We claim:

1. A method to grow and concentrate algae comprising the steps of
    (a) providing a nutritional composition including nutrients for algae;
    (b) preparing an aqueous solution of algae by growing algae in water in a first container while exposing said aqueous solution to sunlight and adding said nutritional composition to the water in said first container, said first container having a bottom;
    (c) preparing an aqueous solution of algal-agglomeration bacteria by growing bacteria in water in a second container;
    (d) admixing said aqueous solution of said algal-agglomeration bacteria to said aqueous solution of algae in said first container to produce an algal-bacterial aqueous solution and continuing to expose said algal-bacterial aqueous solution to sunlight to concentrate algae at said bottom of said first container;
    (e) discontinuing the addition to said first container of said nutritional composition; and
    (f) concentrating algae from said bottom of said container 24 to 48 hours after said algal-agglomeration bacteria is admixed to said aqueous solution of algae in step (d).

* * * * *